(12) United States Patent
Zhang et al.

(10) Patent No.: US 7,914,740 B2
(45) Date of Patent: *Mar. 29, 2011

(54) BIOSENSOR UTILIZING A RESONATOR HAVING A FUNCTIONALIZED SURFACE

(75) Inventors: Yuegang Zhang, Cupertino, CA (US); Andrew A. Berlin, San Jose, CA (US); Qing Ma, San Jose, CA (US); Li-Peng Wang, San Jose, CA (US); Valluri Rao, Saratoga, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/317,405

(22) Filed: Dec. 22, 2005

(65) Prior Publication Data

US 2006/0133952 A1 Jun. 22, 2006

Related U.S. Application Data

(62) Division of application No. 10/749,529, filed on Dec. 30, 2003, now abandoned.

(51) Int. Cl.
*G01N 33/50* (2006.01)

(52) U.S. Cl. ... 422/68.1; 422/50; 422/82.01; 422/82.02; 422/82.03; 422/98; 436/43; 436/86; 436/87; 436/94; 436/501

(58) Field of Classification Search .......... 422/50, 422/68.1, 61, 82.01–82.03, 98; 436/501, 436/43, 63, 86–87, 94–95
See application file for complete search history.

(56) References Cited

U.S. PATENT DOCUMENTS

| 4,596,697 | A | * | 6/1986 | Ballato | 422/98 |
| 4,642,508 | A | * | 2/1987 | Suzuki et al. | 310/321 |
| 4,735,906 | A | | 4/1988 | Bastiaans et al. | |
| 4,789,804 | A | * | 12/1988 | Karube et al. | 310/311 |
| 4,847,193 | A | * | 7/1989 | Richards et al. | 435/6 |
| 4,999,284 | A | * | 3/1991 | Ward et al. | 435/4 |
| 5,129,262 | A | * | 7/1992 | White et al. | 73/599 |
| 5,135,852 | A | * | 8/1992 | Ebersole et al. | 435/39 |

(Continued)

FOREIGN PATENT DOCUMENTS

DE 3733986 * 4/1989

(Continued)

OTHER PUBLICATIONS

O'Toole, R. P. et al, Analytical Chemistry 1992, 64), 1289-1294.*

(Continued)

*Primary Examiner* — Arlen Soderquist
(74) *Attorney, Agent, or Firm* — Pillsbury Winthrop Shaw Pittman LLP

(57) ABSTRACT

Systems and methods for detecting the presence of biomolecules in a sample using biosensors that incorporate resonators which have functionalized surfaces for reacting with target biomolecules. In one embodiment, a device includes a piezoelectric resonator having a functionalized surface configured to react with target molecules, thereby changing the mass and/or charge of the resonator which consequently changes the frequency response of the resonator. The resonator's frequency response after exposure to a sample is compared to a reference, such as the frequency response before exposure to the sample, a stored baseline frequency response or a control resonator's frequency response.

23 Claims, 7 Drawing Sheets

U.S. PATENT DOCUMENTS

| | | | |
|---|---|---|---|
| 5,501,986 | A | 3/1996 | Ward et al. |
| 5,552,274 | A * | 9/1996 | Oyama et al. ............... 435/6 |
| 5,595,908 | A * | 1/1997 | Fawcett et al. ......... 435/287.2 |
| 5,705,399 | A | 1/1998 | Larue |
| 5,789,845 | A * | 8/1998 | Wadaka et al. ............ 310/334 |
| 5,814,525 | A | 9/1998 | Renschler et al. |
| 5,852,229 | A * | 12/1998 | Josse et al. ............. 73/24.06 |
| 5,910,286 | A * | 6/1999 | Lipskier ................. 422/68.1 |
| 5,932,953 | A | 8/1999 | Drees et al. |
| 5,936,150 | A | 8/1999 | Kobrin et al. |
| 5,993,631 | A * | 11/1999 | Parton et al. ............. 204/547 |
| 6,060,818 | A * | 5/2000 | Ruby et al. .............. 310/363 |
| 6,156,578 | A | 12/2000 | Tom |
| 6,218,507 | B1 | 4/2001 | Gao et al. |
| 6,284,475 | B1 * | 9/2001 | Rand .................... 435/7.21 |
| 6,289,286 | B1 | 9/2001 | Andersson et al. |
| 6,329,824 | B1 | 12/2001 | Tsuzuki et al. |
| 6,348,795 | B2 | 2/2002 | Pringle et al. |
| 6,355,498 | B1 * | 3/2002 | Chan et al. ................ 438/48 |
| 6,358,523 | B1 * | 3/2002 | Safinya et al. ............ 424/450 |
| 6,458,599 | B1 * | 10/2002 | Huang .................... 436/518 |
| 6,485,984 | B1 * | 11/2002 | Kim ...................... 436/525 |
| 6,514,767 | B1 | 2/2003 | Natan |
| 6,630,309 | B2 | 10/2003 | Willner et al. |
| 6,842,088 | B2 | 1/2005 | Yamada et al. |
| 6,846,654 | B1 | 1/2005 | Blackburn et al. |
| 6,955,787 | B1 * | 10/2005 | Hanson ................... 422/50 |
| 2002/0008443 | A1 * | 1/2002 | Yamada et al. ............ 310/324 |
| 2002/0067106 | A1 * | 6/2002 | Sunwoo et al. ............ 310/330 |
| 2004/0150296 | A1 | 8/2004 | Park et al. |
| 2005/0101841 | A9 * | 5/2005 | Kaylor et al. ............ 600/300 |
| 2005/0153370 | A1 * | 7/2005 | Lakshmi et al. ........... 435/7.2 |
| 2006/0019373 | A1 * | 1/2006 | Kahlman et al. ........ 435/287.2 |
| 2006/0054941 | A1 * | 3/2006 | Lu et al. .................. 257/252 |
| 2006/0160144 | A1 | 7/2006 | Fendler |

FOREIGN PATENT DOCUMENTS

| | | | |
|---|---|---|---|
| JP | 2002-48797 | * | 2/2002 |
| WO | 87/02066 | * | 4/1987 |
| WO | 2004/017063 | A2 | 2/2004 |

OTHER PUBLICATIONS

Benes, E. et al, Sensors and Actuators, A: Physical 1995, 48, 1-21.*
Naik, R. S. et al, IEEE transactions on ultrasonics, ferroelectrics, and frequency control, 1998, 45, 257-263.*
White, R. M., Proceedings of the IEEE International Frequency Control Symposium 1998, 587-594.*
Linnen, C. et al, SPIE 1999, 3710, 328-334.*
Tait, R. N. et al, Journal of Vacuum Science & Technology, A: Vacuum, Surfaces, and Films 2001, 19, 1586-1590.*
Hauptmann, P. et al, Proceedings—IEEE Ultrasonics Symposium 2003, vol. 1, 56-65.*
Mannelli, I. et al, IEEE Sensors Journal 2003, 3, 369-375.*
Brederlow, R. et al, Technical Digest—International Electron Devices Meeting 2003, 992-994.*
Bayley, H. et al, Nature 2001, 413, 226-230.*
O'Toole, R. P. et al, Analytical Chemistry 1992, 64, 1289-1294.*
Smith, J. H. et al, 8th International Conference on Solid-State Sensors and Actuators, and Eurosensors IX, Jun. 25-29, 1995, 724-727.*
Bodenhofer, K. et al, 8th International Conference on Solid-State Sensors and Actuators, and Eurosensors IX, Jun. 25-29, 1995, 728-731.*
Andle, J. C. et al, IEE Ultrasonics Symposium 1995, 451-460.*
Benes, E et al, IEEE International Frequency Control Symposium 1997, 5-20.*
Lec, R. M. et al, Proceedings of the 20th Annual International Conference of the IEEE Engineering in Medicine and Biology Society, 1998 20, 2779-2784.*
Benes, E. et al, IEEE Transactions on Ultrasonics, Ferroelectrics and Frequency Control 1998, 45, 1314-1330.*
Ketterer, T. et al, Sensors and Actuators B 2000, 65, 73-75.*
Tombelli, S. et al, Analytica Chimica Acta 2000, 418, 1-9.*
Wu, Y. et al, Microchemical Journal 2000, 65, 67-74.*
Lec, R. M., 2001 IEEE International Frequency Control Symposium and PDA Exhibition 2001, 419-429.*
Mansfeld, G. D. et al, IEEE Ultrasonics Symposium 2002, 909-912.*
Hauptmann, P. et al, IEEE Ultrasonics Symposium 2003, 56-65.*
Gabl, R. et al, Sensors, 2003. Proceedings of IEEE Oct. 22-24, 2003, 2, 1184-1188.*
Doering, et al., "Spectroscopic Tags Using Dye-Embedded Nanoparticles and Surface—Enhanced Raman Scattering", *Analytical Chemistry*, :5-9.
Forrer, et al., "Beyond Binding: Using Phage Display to Select for Structure, Folding and Enzymatic Activity in Proteins", *Structural Biology* 9:514-520 (1999).
Gabl et al., "First results on label-free detection of DNA and protein molecules using a novel integrated sensor technology based on gravimetric detection principles", Biosensors & Bioelectronics, vol. 19, 2004, pp. 615-620.
Gabl et al., "Novel Integrated FBAR Sensors: A Universal Technology Platform for Bio- and Gas-Detection", IEEE, vol. 2 of 2, Oct. 2003, pp. 1184-1188.
Kay, et al., "Screening Phage-Displayed Combinatorial Peptide Libraries", *Methods* 24:240-246 (2001).
Lee, et al., "Ordering of Quantum Dots Using Genetically Engineered Viruses", *Sci.* 296:892-895 (May 2002).
Mulvaney, et al., "Glass-Coated, Analyte-Tagged Nanoparticles: A New Tagging System Based on *Detection* with Surface-Enhanced Raman Scattering", *Am Chem Soc.* 19:4784-4790 (2003).
Seeman, et al., "Emulating Biology: Building Nanostructures from the Bottom Up", PNAS Early Edition, www.pnas.org/cgi/doi/10.1073/pnas.221458298.
Ulman, Abraham, "Formation and Structure of Self-Assembled Monolayers", *Chem. Rev.* 96:1533-1554, (1996).
Whaley, et al., "Selection of Peptides with Semiconductor Binding Specificity for Directed Nanocrystal Assembly", *Nature* 405:665-668 (Jun. 2000).
Zhang et al., "A novel piezoelectric quartz micro-array immunosensor based on self-assembled monolayer for determination of human chorionic gonadotropin", Biosensors & Bioelectronics, vol. 19, 2004, pp. 711-720.

* cited by examiner

BIOSENSOR UTILIZING A RESONATOR HAVING A FUNCTIONALIZED SURFACE

CROSS REFERENCE TO RELATED APPLICATIONS

This application is a divisional application of U.S. Ser. No. 10/749,529 filed Dec. 30, 2003, now abandoned. The disclosure of the prior application is considered part of and is incorporated by reference in the disclosure of this application.

BACKGROUND OF THE INVENTION

1. Field of the Invention

The invention relates generally to biosensors, and more particularly to biosensors that incorporate resonators having functionalized surfaces for binding or otherwise reacting with target biomolecules in a manner that changes the frequency responses of the resonators.

2. Background Information

Biosensors are used to detect the presence and/or levels of biomolecules, typically in a fluid sample. For instance, biosensors may be used to determine the levels of particular chemicals in biological fluids, such as blood. Specific sensors can therefore be used to determine the levels of glucose, potassium, calcium, carbon dioxide, and other substances in blood samples.

Biosensors such as these often use an electrochemical system to detect a particular substance of interest. The electrochemical system includes substances such as enzymes and redox mediators to react with the substance of interest (the target substance) and to thereby produce ions that can carry a current. A set of electrodes are used to generate an electrical potential that attracts the ions to the electrodes, creating a circuit that can be used to measure the resulting current.

In one type of system, a biosensor includes an enzyme which is immobilized by a membrane. The target substance in a fluid sample migrates through the membrane and reacts with the enzyme. This forms ions within the fluid sample. These ions then migrate through the fluid sample to the system's electrodes. The migration of the ions to the electrodes generates an electrical current that is measured. Because the current depends upon the concentration of the target substance in the sample, the measured current is then translated to a concentration of the target substance.

There are a number of problems with these conventional biosensors. For example, they are relatively slow. This is, at least in part, a result of the fact that it is necessary in electrochemical biosensors to allow a certain amount of time to pass before the current resulting from the ionization of the target substance in the sample is established. Only after this current is allowed to establish itself can it be measured to provide a reasonably accurate estimate of the concentration of the target substance.

Even after the current resulting from the ionization of the target substance is established and measured, the resulting estimation of the target substance concentration typically is not as accurate as would be desirable. This is a result, at least in part, of the fact that the sample being tested typically contains various other substances, some of which may interfere in the process. For instance, some of these other substances may ionize in the sample and thereby increase the measured current, leading to an overestimation of the target substance concentration. Alternatively, some chemicals may react with the ions of the target substance, thereby reducing the measured current and causing an underestimation of the target substance concentration.

It would therefore be desirable to provide systems and methods that enable the testing of samples to determine the presence of target substances more quickly and more accurately than is typically possible using prior art systems and methods.

BRIEF DESCRIPTION OF THE DRAWINGS

Other objects and advantages of the invention may become apparent upon reading the following detailed description and upon reference to the accompanying drawings.

Figure 1:
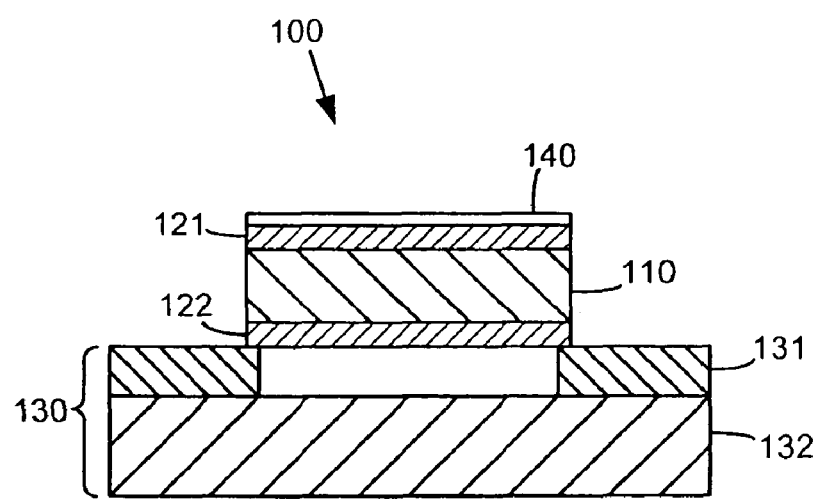
FIG. 1 is a diagram illustrating the structure of an exemplary resonator in accordance with one embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiments which are described. This disclosure is instead intended to cover all modifications, equivalents and alternatives falling within the scope of the present invention as defined by the appended claims.

DETAILED DESCRIPTION OF PREFERRED EMBODIMENTS

One or more of the problems outlined above may be solved by the various embodiments of the invention. Broadly speaking, the invention comprises systems and methods for detecting the presence of molecules (e.g., biomolecules) in a sample using sensors that incorporate resonators which have functionalized surfaces for binding or otherwise reacting with target molecules in a manner that changes the frequency responses of the resonators.

In one embodiment of the invention, a device includes a resonator, where the resonator has at least one functionalized surface which is configured to react with target molecules. The reaction of the target molecules with the functionalized surface causes changes in the mass and/or charge of the resonator, stress/strain, surface energy/tension and the like, which cause changes in the vibrational characteristics of the resonator. Changes in the vibrational characteristics of the resonator may be manifested through corresponding changes in electrical characteristics of the resonator.

In one embodiment, the resonator consists of a layer of piezoelectric material and a pair of electrodes that are coupled to opposite sides of the layer of piezoelectric material. One of the electrodes forms the functionalized surface of the resonator. When an excitation signal is applied across the electrodes, the frequency response of the resonator can be determined. When target biomolecules come into contact with the functionalized surface, the target biomolecules react (e.g., bind) with the functionalized surface and cause changes in the mass and/or electrostatic charge of the resonator. By determining the frequency responses of the resonator before and after exposure to a sample that may contain target biomolecules, changes in the frequency response correlated to the changed mass and/or electrostatic charge can be determined, indicating the detection of the target biomolecules.

In one embodiment, a pair of resonators is used. Each of the resonators is essentially as described above, except that one of the resonators has a functionalized surface and the other does not. The resonator that does not have a functionalized surface is used as a control against which the other resonator can be compared. Thus, when both resonators are exposed to a sample, any target biomolecules will affect the frequency response of the functionalized-surface resonator, but not the resonator without the functionalized surface. Any non-target molecules will equally affect both resonators and the corresponding frequency responses, so a comparison of the two resonators will effectively cancel out any effects resulting from non-target molecules.

In one embodiment of the invention, a method includes the steps of providing a resonator having a surface functionalized with a type of biomolecules, where the presence of target molecules causes the biomolecules of the functionalized surface to change the frequency response of the resonator, exposing the functionalized surface of the resonator to a test fluid, determining a frequency response of the resonator after the functionalized surface has been exposed to the test fluid, and determining whether the test fluid contains target molecules based upon the frequency response of the resonator.

In one embodiment, the method includes the additional steps of providing a second resonator that does not have a functionalized surface, exposing the second resonator to the test fluid, determining a frequency response of the second resonator after the second resonator has been exposed to the test fluid, and comparing the frequency response of the second resonator to the frequency response of the first (functionalized) resonator to determine the effect of target molecules on the frequency response of the first resonator.

Numerous additional embodiments are also possible.

One or more embodiments of the invention are described below. It should be noted that these and any other embodiments described below are exemplary and are intended to be illustrative of the invention rather than limiting.

As described herein, various embodiments of the invention comprise systems and methods for detecting the presence of molecules in a sample using sensors that incorporate resonators which have functionalized surfaces for binding or otherwise reacting with target molecules in a manner that changes the frequency responses of the resonators.

In one embodiment, a biosensor includes a piezoelectric resonator that has a surface which is functionalized to react with target biomolecules. The resonator consists in one embodiment of a layer of piezoelectric material that has a pair of electrodes that are coupled to opposite sides of the layer of piezoelectric material. One of the electrodes forms the functionalized surface of the resonator. When an excitation signal is applied across the electrodes, the frequency response of the resonator can be determined. When target biomolecules come into contact with the functionalized surface, the target biomolecules react (e.g., bind) with the functionalized surface and cause changes in the mass and/or electrostatic charge of the resonator. By determining the frequency responses of the resonator before and after exposure to a sample that may contain target biomolecules, changes in the frequency response correlated to the changed mass and/or electrostatic charge can be determined, indicating the detection of the target biomolecules.

In one embodiment, a pair of resonators is used. Each of the resonators is essentially as described above, except that one of the resonators has a functionalized surface and the other does not. The resonator that does not have a functionalized surface is used as a control against which the other resonator can be compared. Thus, when both resonators are exposed to a sample, any target biomolecules will affect the frequency response of the functionalized-surface resonator, but not the resonator without the functionalized surface. Any non-target molecules will equally affect both resonators and the corresponding frequency responses, so a comparison of the two resonators will effectively cancel out any effects resulting from non-target molecules.

Referring to FIG. 1, a diagram illustrating the structure of an exemplary resonator in accordance with one embodiment is shown. The resonator illustrated in this figure comprises a film bulk acoustic resonator (FBAR) device. Device 100 includes a layer of piezoelectric material 110 sandwiched between electrodes 121 and 122 to form a resonator component. This resonator component is positioned with its edges on a silicon/silicon dioxide substrate 130 (a layer of silicon dioxide 131 deposited on a layer of silicon 132) in order to allow the resonator component to vibrate. The exposed surface of electrode 121 is functionalized with a layer 140 of biologically active or derivatized material. The biologically active or derivatized material interacts with the target biomolecules by, for example, binding the biomolecules to layer 140 and thereby changing the mass or electrostatic charge of this layer and, consequently, the resonator component.

The FBAR resonator may be constructed using techniques that are known to persons of skill in the art. For example, in one embodiment, a FBAR resonator may be constructed according to the following process.

First, a substrate is provided. In one embodiment, a silicon wafer is used as the substrate, although other substrate materials used in semiconductor processing (e.g., gallium arsenide) can also be used. A layer of sacrificial material is then deposited on the substrate. The sacrificial layer may consist of a variety of materials, such as Al, Cu, NiFe, ZnO, or other suitable materials that are known in the art. The sacrificial layer may be deposited using any suitable process, such as sputtering or vapor deposition.

A photoresist layer is then formed on top of the sacrificial layer. A pattern is then formed in the photoresist using conventional methods. The patterned photoresist forms a mask which is used to selectively etch the sacrificial layer. More specifically, the photoresist mask covers an area of the sacrificial layer that will later form an air gap beneath the piezoelectric resonator component. After the sacrificial layer is etched, an insulator layer is deposited on the substrate, effectively replacing the sacrificial layer that was previously etched away. The insulator layer can be deposited or otherwise formed using conventional means.

After the insulator layer is deposited, the photoresist is removed using, for example, a lift-off process. The portion of the insulator layer that is on top of the photoresist is also removed. This results in a patterned layer of insulator and sacrificial materials on top of the substrate. In other words, the sacrificial material is inset within the insulator material (or vice versa) to form a pattern within this layer. This layer will form the supporting structure for the resonator component after the sacrificial material is removed in a later step.

A membrane layer may optionally be formed on top of the patterned insulator/sacrificial layer. References below to formation of structures on top of the layer of insulator/sacrificial material should be construed as formation of the structures on the membrane layer if the membrane layer is used.

A conductive layer is then formed on the layer of insulator/sacrificial material. This conductive layer may consist of any conductive material such as a metal. Suitable metals may include Al, Au, W, Pt or Mo. This conductive layer is patterned to form a lower electrode of the resonator component. A layer of piezoelectric material, such as AlN or ZnO, is then formed on top of the conductive layer. This piezoelectric layer is patterned to form the body of the piezoelectric resonator. A second conductive layer is then formed on top of the piezoelectric layer. This conductive layer is patterned to form the upper electrode of the resonator component. After the resonator component is formed in this manner, the sacrificial material on the substrate below the resonator component is removed using, for example, a wet etch process (it may be necessary to form a via to the sacrificial layer in order to effect the removal of this material).

The upper electrode of the resonator component has a lower side which is bound to the piezoelectric layer and an upper side which is exposed. This exposed to surface is then functionalized so that it will react (e.g., bound) with target molecules. In one embodiment, the electric surface is functionalized with antibody or DNA molecules. This may be accomplished by forming self-assembling monolayers of various thiols or sulfides on the electrode surface using a chemisorption process. The antibody or DNA molecules can then be covalently linked to the self-assembled monolayer using an activation process.

Various alternative means for functionalizing the surface of the resonator are also possible. For example, the functionalization of the FBAR device may be achieved by immobilization of biomolecules on an organic membrane that is pre-coated on the surface of the device, or chemically derivatized such as silylation, esterification, alkylation, or similar processes that are known in the art. The functionalization of the FBAR device may also be achieved by direct immobilization of biomolecules on a metal or other inorganic film on the surface of the device, or self-assembled biomolecular layers such as amino acid-derivatized fatty acids/lipids on the surface of the device.

Because the biosensor may be used in a "wet" environment, it may be necessary to protect portions of the biosensor other than the exposed resonator surfaces. In other words, the sample which is being tested to determine the presence of the target biomolecules may be a liquid sample. For some of the components of the biosensor, exposure to a liquid sample may cause problems that could prevent proper operation of the biosensor. For example, the liquid sample could cause a short circuit between the electrodes of the resonator component, thereby preventing measurement of changes in the frequency response of the resonator. Some embodiments of the invention may therefore also include a protective layer that covers the components of the biosensor, except for the functionalized surface of the resonator component (and possibly the non-functionalized electrode surface of a corresponding control biosensor). This protective layer may be provided by forming a polymer membrane over the components that require protection.

Figure 6:
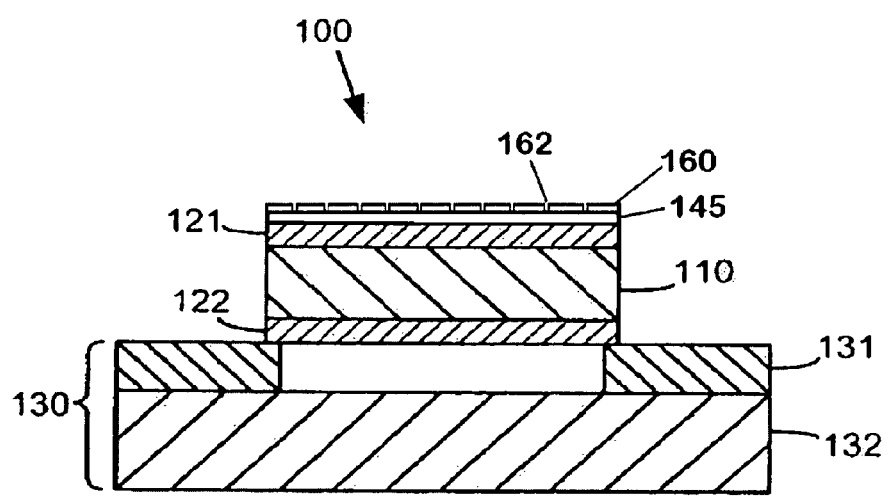
FIG. 6 is a diagram illustrating the structure of an exemplary resonator in accordance with one embodiment.

It should be noted that the foregoing description pertains to a single, exemplary embodiment. Alternative embodiments may be formed using slightly different steps in the described process. A number of these variations are included in the description of the foregoing process, and additional such variations will be apparent to those of skill in the art upon reading the present disclosure. For example, in one alternative embodiment (FIG. 6), the exposed electrode surface of the resonator component may be functionalized by coating the surface with an ion-selective membrane 145. The ion-selective membrane 145 can then be functionalized with enzymes such as glucose oxidase. Alternatively, the ion-selective membrane can be functionalized with a functional membrane 160 that provides transport mechanisms 162 such as carrier molecules, ion pores or channels extracted from biological materials or synthetic biochemicals.

As noted above, the FBAR biosensor described herein is used by detecting changes in the frequency response of the resonator that result from the exposure of the biosensor to a sample and subsequent reaction of the functionalized surface with the target molecules. In order to determine the frequency response of the resonator, control circuitry is provided. An exemplary embodiment of a system including an FBAR biosensor and corresponding control electronics is shown in FIG. 2.

Figure 2:
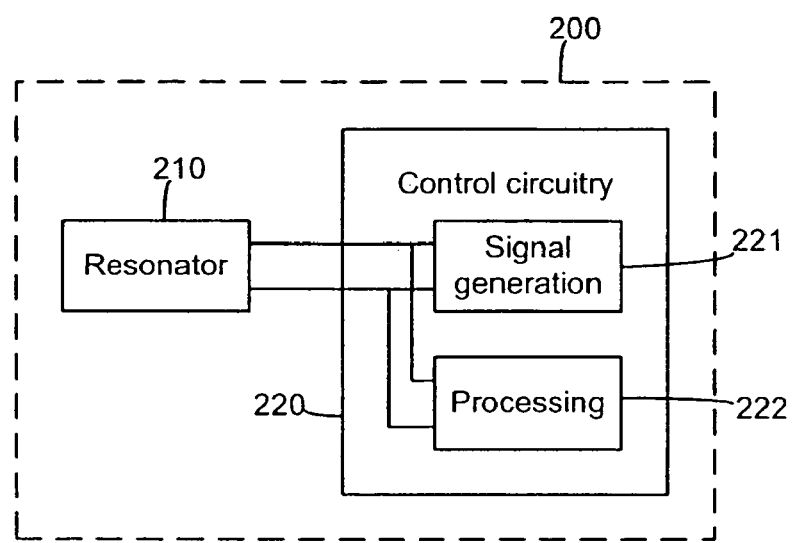
FIG. 2 is a functional block diagram illustrating a biosensor system in accordance with one embodiment.

Referring to FIG. 2, a functional block diagram illustrating a biosensor system in accordance with one embodiment is shown. In this embodiment, system 200 includes a resonator 210 and control the circuitry 220. In one embodiment, resonator 210 is as described above. Resonator 210 is coupled to control circuitry 220 by the electrodes of the resonator. The electrodes are coupled to signal generation circuitry 221 and processing circuitry 222 components of control circuitry 220.

Signal generator circuitry 221 is configured to produce an excitation signal that is applied to the electrodes of resonator 210. The excitation signal has an AC (alternating current) component that causes the piezoelectric material of the resonator to vibrate. Because of the physical characteristics of resonator 210, the resonator has a characteristic frequency response. The frequency response of resonator 210 manifests itself in the variability of the electrical characteristics of the resonator (e.g., the impedance of the resonator). These electrical characteristics can be measured by processing circuitry 222.

The frequency response of resonator 210 has a fundamental resonance at a frequency at which the corresponding wavelength is twice the thickness of the resonator. The wavelength is equal to the acoustic velocity of the piezoelectric material, divided by the frequency. The acoustic velocity of the piezoelectric material depends upon the specific material that is used. For instance, AlN has an acoustic velocity of about 10,400 meters per second, while ZnO has an acoustic velocity of about 6,330 meters per second. Thus, for a resonator using AlN, if the thickness of the resonator is about 2.5 micrometers, the resonant frequency is about 2 GHz. If it is desired to adjust the resonant frequency to a different frequency, this can be achieved by, for example, changing the piezoelectric material or changing the thickness of the resonator.

It should be noted that, because the technology used in the manufacturing of FBAR devices is compatible with both Si and GaAs wafer processing techniques, it is possible to combine these technologies to make all-in-one biosensors. In other words, it is possible to manufacture both the resonator and the control circuitry on a single chip. This may provide additional advantages over the prior art in terms of simplification of the design of the respective components of the biosensors, improved power efficiency, and so on.

Thus, in one embodiment, biosensor system 200 operates by generating an excitation signal that includes a plurality of frequencies (not necessarily at the same time), applying this excitation signal to resonator 210 and then measuring the electrical characteristics of the resonator corresponding to each of the frequencies. For example, signal generator circuitry 221 may generate an excitation signal that includes a single frequency which varies as a function of time. In other words, signal generator circuitry 221 scans through a range of frequencies. Processing circuitry 222 may then measure, for example, the impedance across resonator 210 as a function of frequency (which is a function of time). This frequency response (i.e., the impedance of resonator 210 as a function of frequency) may be digitized, stored and compared to a baseline response, or in may be compared to the response of a control resonator, which would be operated in the same manner.

It should be noted that the excitation signal applied to the resonator may include various components (e.g., single or mixed frequencies, or time-variant components). Similarly, the frequency response may be measured in terms of various response components (e.g., in-phase and out-of-phase components) or other response characteristics. Such response characteristics may include the steady-state frequency shifts of the resonators due to changes of mass or electrostatic charge resulting from the specific binding of the target molecules with the immobilized biomolecules on the resontaors' surfaces (e.g., antibody-antigen, DNA hybridization, molecular receptor binding, molecular configurational changes).

The biosensor is useful in the detection of target molecules because, in reacting with the functionalized surface of the resonator, the target molecules change the mass and/or electrostatic charge of the resonator, both of which affect the resonance of the resonator. In other words, these characteristics change the vibrational characteristics of the resonator. For example, if the target molecules bind with the functionalized surface and thereby effectively increase the mass of the resonator, the resonator will tend to respond less quickly to the forces generated by the applied excitation signal. The resonant frequency will therefore be lower. Thus, if, prior to the binding of target molecules to the functionalized surface, a resonator resonates at a frequency f, the additional mass of the target molecules that are bound to the functionalized surface will cause the resonator to resonate at a frequency f-$\Delta$f. If the frequency response of the resonator is viewed as a function of frequency, this corresponds to a shift of the peak response to the left (the lower frequencies).

Figure 3A:
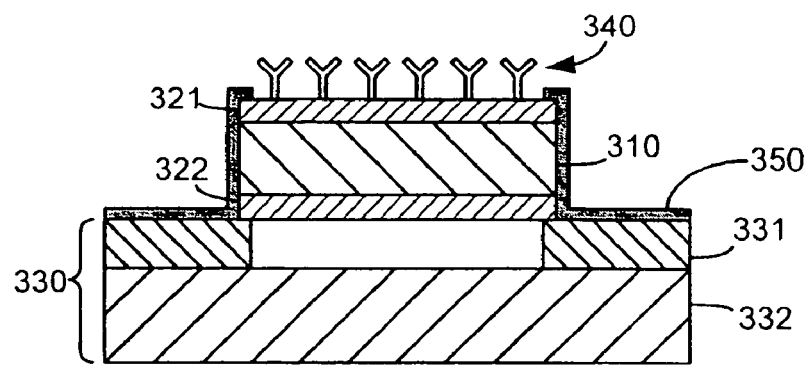
FIGS. 3A-3C are a set of diagrams illustrating the binding of target molecules to the functionalized surface of a biosensor in accordance with one embodiment.
Figure 3B:
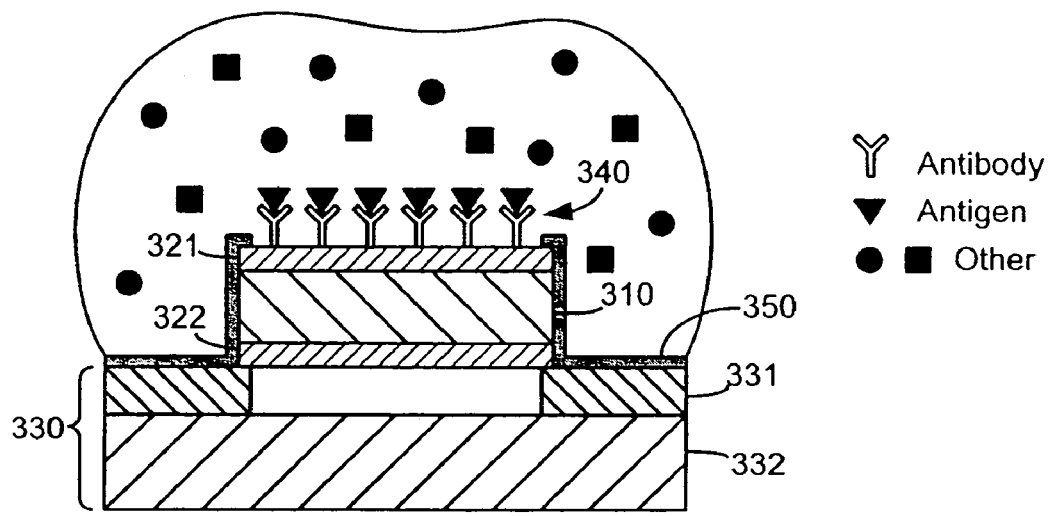
Figure 3C:
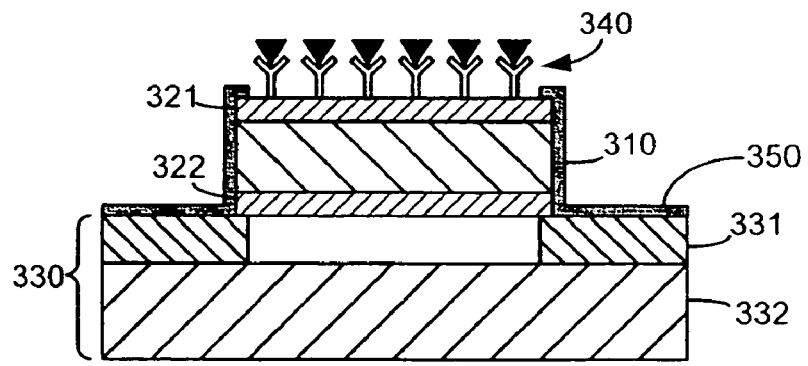

Referring to FIGS. 3A-3C, a set of diagrams illustrating the binding of target molecules to the functionalized surface of a biosensor in accordance with one embodiment shown. Referring first to FIG. 3A, a diagram illustrating a biosensor prior to exposure to a sample is shown. The biosensor has essentially the same structure shown in FIG. 1, including a support structure formed by substrate 331 and insulator layer 332, and a resonator component formed by piezoelectric layer 310 sandwiched between electrodes 321 and 322. Electrode 322 of the resonator component is functionalized by antibodies 340, which can be bound to the electrode, for example, by a self-assembling monolayer of a thiol. A protective polymer layer 350 (not shown in FIG. 1) covers the resonator component and support structure, except for the functionalized surface of the resonator component.

Referring next to FIG. 3B, a diagram illustrating the biosensor of FIG. 3A during exposure to a sample is shown. As depicted in this figure, sample 360 contains a variety of different biomolecules, including antigen molecules (target molecules, represented in the figure by triangles) and various other molecules (non-target molecules, represented in the figure by circles and squares). The biomolecules are distributed throughout sample 360, so that some of the biomolecules come into contact with the functionalized surface of the biosensor. As the biomolecules come into contact with the functionalized surface, they may or may not become bound to the functionalized surface. More specifically, if a biomolecule that comes into contact with the functionalized surface is an antigen corresponding to the antibodies of the functionalized surface, it will be bound to one of the antibodies. If the biomolecule is not the specific antigen corresponding to the antibodies, it will not be bound to the antibodies of the functionalized surface.

Referring next to FIG. 3C, a diagram illustrating the biosensor of FIGS. 3A and 3B after the sample is removed is shown. It can be seen from this figure that, when the sample (e.g., a biological fluid) is removed from the biosensor, the non-antigen biomolecules contained in the sample are also removed. The antigen biomolecules bound to the antibodies remain. These antigens affect the mass and/or electrostatic charge of the resonator component and will therefore change the frequency response of the resonator component. Thus, the presence of the antigen biomolecules is detected by determining whether the frequency response of the resonator component has changed. This is accomplished as described above.

It should be noted that, in some cases, removal of the sample from the biosensor may not ensure that all of the non-target biomolecules have been removed from the functionalized surface of the resonator component. These non-target molecules may affect the frequency response of the resonator component and consequently affect the determination of whether target molecules were present in the sample. In one embodiment, the effect of these non-target molecules is compensated for through the use of a control biosensor in addition to the test biosensor. The control biosensor is essentially identical to the test biosensor, except that the surface of the resonator component is not functionalized to react with the target biomolecules. When the sample is tested, both the test biosensor and control biosensor are exposed to the sample. Any non-target molecules that are not removed from the test biosensor should likewise not be removed from the control biosensor. Because the control biosensor does not bind the target biomolecules, any change in the frequency response of the resonator component of the control biosensor should be due to the presence of these non-target biomolecules. Since the effect of the non-target biomolecules is known from the frequency response of the control biosensor, this effect can effectively be "subtracted out" of the changes in the frequency response of the test biosensor.

It should be noted that, while the foregoing example describes the use of two biosensors (a test biosensor and a control biosensor), the two biosensors may be considered either separate units, or parts of the same biosensor. The two biosensors may each have their own control circuitry, or they may share all or part of the control circuitry. In the latter instance, the example may be more easily understood if the term "biosensor" is replaced with the term "resonator." Both instances are within the scope of the invention.

Figure 4:
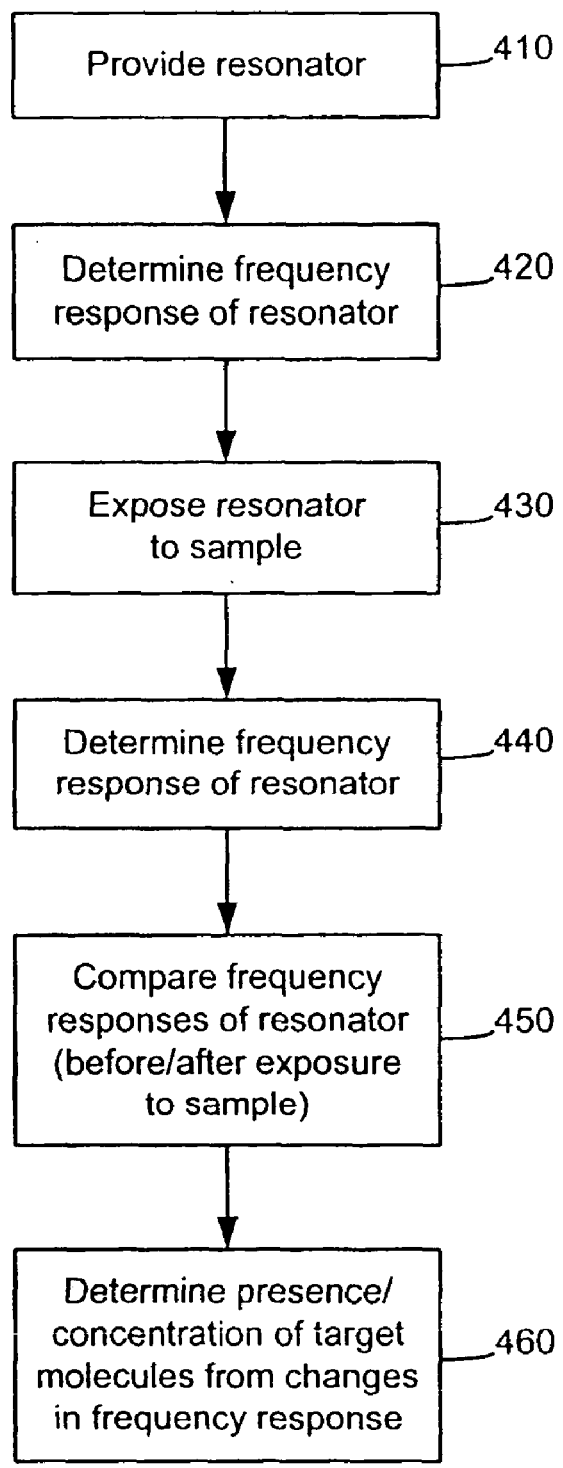
FIG. 4 is a flow diagram illustrating a method for detecting the presence of target molecules in a sample in accordance with one embodiment.

Referring to FIG. 4, a flow diagram illustrating a method for detecting the presence of target molecules in a sample in accordance with one embodiment is shown. In this embodiment, a biosensor having a single resonator is used. The resonator has a functionalized surface that will react with target molecules in a sample. The method of this embodiment includes the steps of providing a resonator having a functionalized surface (block 410), determining the frequency response of the resonator prior to exposure to a sample (block 420), exposing the resonator to the sample (block 430), determining the frequency response of the resonator following exposure to the sample (block 440), comparing the frequency responses of the resonator prior to and following exposure to the sample (block 450), and determining the presence of target molecules based upon changes in the frequency response of the resonator resulting from exposure to the sample (block 460).

A single resonator is employed in this method, and it is necessary to provide a baseline frequency response from which changes in the frequency response can be determined. This baseline is provided in one embodiment by determining the frequency response of the resonator prior to exposure to the sample. In an alternative embodiment, the baseline may be provided by testing a plurality of resonators that are identically manufactured and establishing a composite frequency response, or an average frequency response for resonators having an identical design. In such embodiment, the composite or average frequency response can be stored in a memory coupled to the processing circuitry so that it can be retrieved and compared to the measured frequency response of the resonator after exposure to the sample. Various other means for providing the baseline are also possible.

Figure 5:
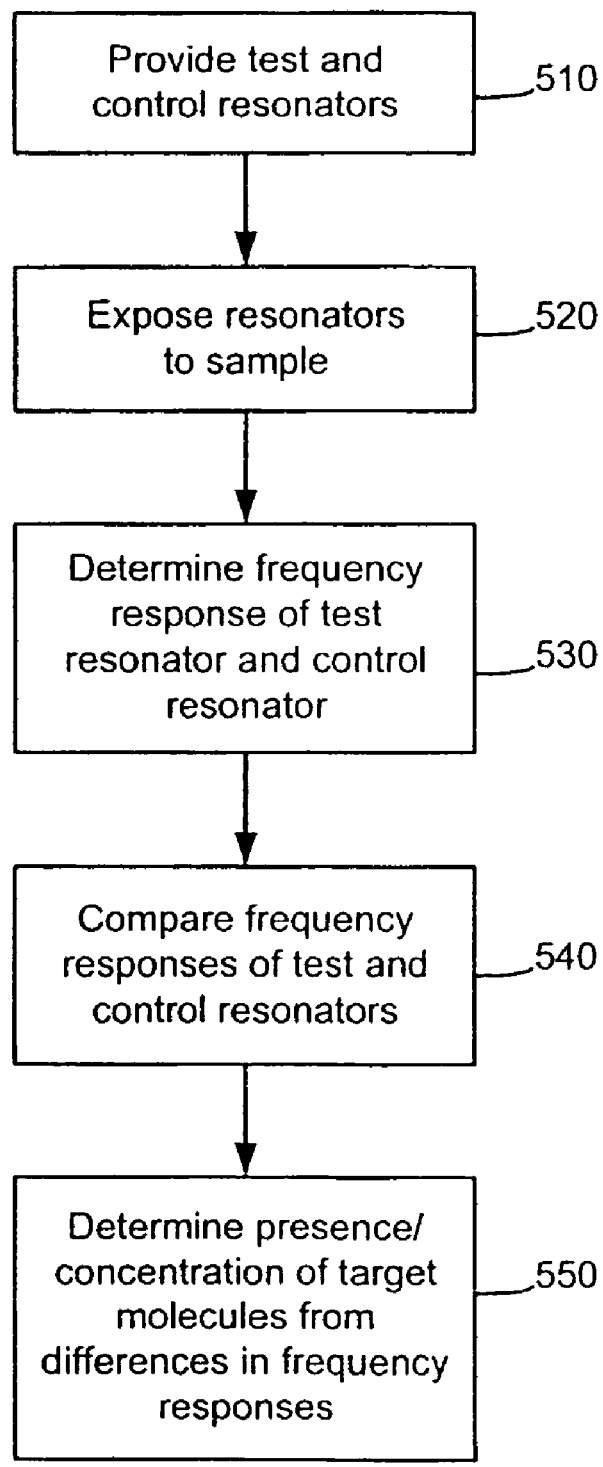
FIG. 5 is a flow diagram illustrating a method for detecting the presence of target molecules in a sample in accordance with an alternative embodiment.

Referring to FIG. 5, a flow diagram illustrating a method for detecting the presence of target molecules in a sample in accordance with an alternative embodiment is shown. In this embodiment, a biosensor having a pair of resonators is used. One of the resonators functions as a test resonator, while the other functions as a control resonator. As described above, the test resonator has a functionalized surface, while the control resonator does not. The signal generation circuitry and processing circuitry for determining the frequency response of each of these resonators may be common. That is, a single set of signal generation and processing circuitry can be used in conjunction with both of the resonators. Alternatively, each resonator may have separate signal generation and processing circuitry.

This alternative method includes the steps of providing a biosensor having dual (test and control) resonators (block 510), exposing the resonator to the sample (block 520), determining the frequency response of the test resonator and the control resonator following exposure to the sample (block 530), comparing the frequency responses of the test resonator and control resonator (block 54), and determining the presence of target molecules based upon differences in the frequency responses of the test resonator and control resonator (block 550.

While this alternative method determines the presence of target molecules based upon differences between the frequency response of a test resonator and the frequency response of a control resonator, it may also be useful to be able to compare either or both of these frequency responses to a baseline response. For instance, even though the resonators may be identically designed (except for non-functionalized surface of the control resonator), the change in frequency response due to the presence of target molecules may not be linear. Therefore, it may be helpful to know not only the magnitude of the difference between the test and control frequency responses, but also the magnitude of the frequency response changes resulting from non target molecules (i.e., the difference between a baseline, pre-sample-exposure frequency response and the control frequency response).

Figure 7:
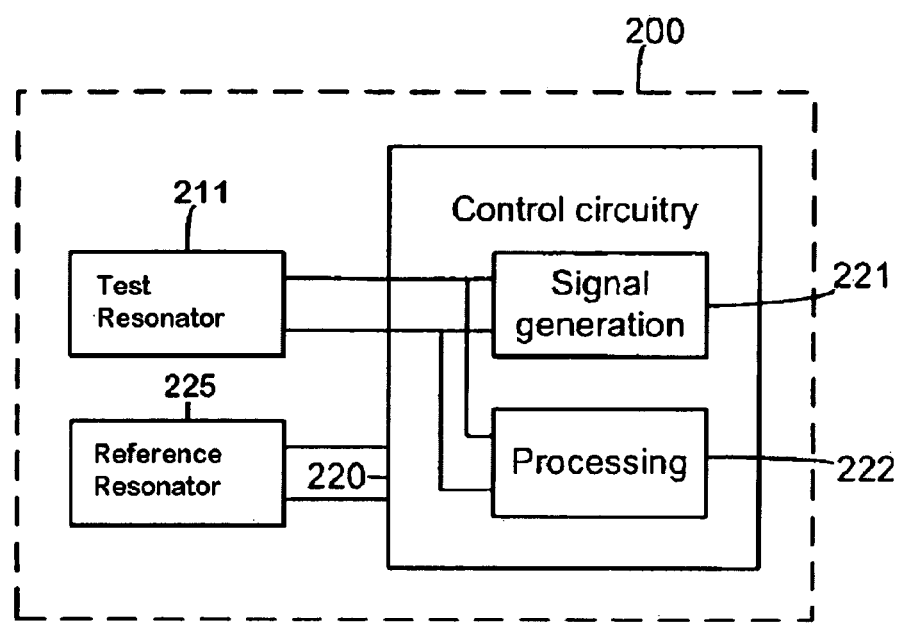
FIG. 7 is a functional block diagram illustrating a biosensor system in accordance with on embodiment.

The embodiment illustrated in FIG. 7 includes a pair of resonators, a test resonator 211, and a reference resonator 225. The test resonator 211 and the reference resonator 225 is essentially as described above except that test resonator 211 has a functionalized surface while the reference resonator 225 does not. The reference resonator 225 is used as a control against which the test resonator 211 can be compared. Thus, when both the test resonator 211 and the reference resonator 225 are exposed to a sample, any target biomolecules will affect the frequency response of the test resonator 211, but not the reference resonator 225. Any non-target molecules will equally affect both the test resonator 211 and the reference resonator 225 and the corresponding frequency responses, so a comparison of the test resonator 211 and the reference resonator 225 will effectively cancel out any effects resulting from non-target molecules.

As noted above, the various embodiments of the present invention may provide a number of advantages over the prior art. These advantages may include greater sensitivity and faster response time than other types of biosensors, higher resonance frequencies that may provide higher sensitivity to changes in mass or in stiffness (resulting from changes in charge), simpler structures than other types of resonators (e.g., single-crystal quartz microbalance or SAW resonators), better power handling characteristics at high frequencies, sharper response peaks (due to reduced parasitic effects, larger surface areas for detection of target molecules, and the ability to perform detection of target molecules during or after exposure to wet environments. Another advantage of some of the embodiments of the present invention is that they may make use of relatively mature technologies (e.g., relating to methods for designing and manufacturing FBAR devices and integrated circuits, or functionalizing various surfaces) and may therefore present fewer difficulties in the design, practice and/or manufacture of the respective embodiments.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A system for the detection of a target molecule in a solution comprising: a substrate, on which is attached a pair of film bulk acoustic resonators (FBARs) consisting of a test FBAR and a reference FBAR, each FBAR comprising a layer of piezoelectric material sandwiched between two electrodes, wherein at least one electrode of each FBAR has an exposed surface and the exposed surface of the test FBAR electrode comprising a layer of functionalized biomolecules that react with the target molecule;

each said FBAR being mounted on an insulator comprising a semiconductive layer and first and second, spaced apart insulating layers, said FBAR having a first edge contacting said first insulating layer and a second edge contacting said second insulating layer, wherein said semiconductive layer, said spaced apart insulating layers, and said FBAR define a void region therebetween, and a control circuit comprising a signal generator circuit that applies an excitation signal having a plurality of frequencies to the two electrodes of each of the pair of FBARs, and a processing circuit that measure and compare the impedances of the test and reference FBARs to the frequencies of the excitation signal, such that a mass, or an electrostatic charge or both, of the target molecules that have specifically reacted with the biomolecules causes a difference between the impedances of test and reference FBARs,
wherein the system is configured to detect the target molecules comprising biological molecules in a liquid sample.

2. The system of claim 1, wherein the excitation signal comprises a time variant, single frequency signal, whereby the plurality of frequencies of the excitation signal are applied sequentially.

3. The system of claim 1, wherein the excitation signal comprises a mixed frequency signal, whereby the plurality of frequencies are applied simultaneously.

4. The system of claim 1 wherein the FBARs are AlN or ZnO FBARs.

5. The system of claim 1 wherein each FBAR is attached to the substrate at its edges, whereby each electrode has an exposed surface.

6. The system of claim 5, further comprising a protective polymer layer that prevents exposure to the solution containing the target molecule of an area comprising at least the exposed surface of one electrode of each of the pair of FBARs and excluding the functionalized electrode surface of the test FBAR.

7. The system of claim 1, wherein the layer of functionalized biomolecules provides a transport mechanism.

8. The device of claim 7, wherein the transport mechanism comprises one or more of carrier molecules, ion pores, or channels.

9. The system of claim 1, wherein the biomolecules comprise an enzyme.

10. A device for detecting target biological molecules comprising:
a film bulk acoustic piezoelectric resonator (FBAR) comprising:
a substrate;
a pair of electrodes;
piezoelectric material that is sandwiched between, and coupled to, the pair of electrodes; and
a protective layer;
said FBAR being mounted on an insulator comprising a semiconductive layer and first and second, spaced apart insulating layers, said FBAR having a first edge contacting said first insulating layer and a second edge contacting said second insulating layer, wherein said semiconductive layer, said spaced apart insulating layers, and said FBAR define a void region therebetween,
wherein the FBAR is configured to generate bulk acoustic waves,
wherein the FBAR is solidly mounted with edges of the FBAR on the substrate,
wherein at least one of the electrodes contains at least one functionalized surface that is configured to react with the target biological molecules, and
wherein the FBAR is configured to be used in a wet environment with the protective layer substantially covering the FBAR and a portion of the substrate, except for the at least one functionalized surface.

11. The device of claim 10, wherein the piezoelectric material is AlN or ZnO.

12. The device of claim 10, wherein the excitation signal comprises an in-phase signal, an out-of-phase signal, a time variant, single frequency signal, a mixed frequency signal, or a time-variant, mixed frequency signal.

13. The device of claim 10, wherein the functionalized surface comprises one or more biomolecules configured to bind with the target molecules, wherein the biomolecules comprise biologically active molecules or biologically derivatized molecules.

14. The device of claim 10, wherein the functionalized surface is functionalized by immobilization of biomolecules on a self-assembly monolayer or an organic membrane that is pre-coated onto the functionalized surface or is chemically derivatized on the functionalized surface.

15. The device of claim 14, wherein the organic membrane is chemically derivatized on the functionalized surface by silylation, acylation, esterification or alkylation.

16. The device of claim 10, wherein the functionalized surface is functionalized by direct immobilization of biomolecules on a metal or a non-metallic inorganic film.

17. The device of claim 10, wherein the functionalized surface is functionalized by self-assembling biomolecular layers on the functionalized surface.

18. The device of claim 17, wherein the self-assembling biomolecular layers comprise amino acid derivatized fatty acids or lipids.

19. The device of claim 10, further comprising a second piezoelectric resonator and an additional pair of electrodes having a non-functionalized surface coupled to the second piezoelectric resonator, wherein the control circuitry is configured to apply the excitation signal to the additional pair of electrodes and to determine a frequency response for the second piezoelectric resonator.

20. The device of claim 10, wherein the FBAR has a resonant frequency in a gigahertz range.

21. The device of claim 10, wherein the FBAR has the resonant frequency of about 2 GHz.

22. The device of claim 10, further comprising a control circuitry comprising: a signal generator configured to apply an excitation signal that includes a plurality of frequencies to the pair of electrodes, and processing circuitry configured to determine an impedance of the FBAR as a function of frequency, such that a mass, or an electrostatic charge or both, of the target biological molecules that have reacted with the functionalized surface causes a detectable change in a frequency response of the FBAR.

23. A system for the detection of a target molecule in a solution comprising: a substrate, on which is attached a pair of film bulk acoustic resonators (FBARs) consisting of a test FBAR and a reference FBAR, each FBAR comprising a layer of piezoelectric material sandwiched between two electrodes, wherein at least one electrode of each FBAR has an exposed surface and the exposed surface of the test FBAR electrode comprising the exposed surface of the test FBAR electrode comprising a functional membrane;
said FBAR being mounted on an insulator comprising a semiconductive layer and first and second, spaced apart insulating layers, said FBAR having a first edge contacting said first insulating layer and a second edge contacting said second insulating layer, wherein said semiconductive layer, said spaced apart insulating layers, and said FBAR define a void region therebetween,
and
a control circuit comprising a signal generator circuit that applies an excitation signal having a plurality of frequencies to the two electrodes of each of the pair of FBARs, and a processing circuit that measure and compare the impedances of the test and reference FBARs to the frequencies of the excitation signal, such that a mass, or an electrostatic charge or both, of the target molecules that have specifically reacted with the biomolecules causes a difference between the impedances of test and reference FBARs,
wherein the system is configured to detect the target molecules comprising biological molecules in a liquid sample.

* * * * *